US012083139B2

(12) United States Patent
Alberini et al.

(10) Patent No.: US 12,083,139 B2
(45) Date of Patent: Sep. 10, 2024

(54) USE OF IGF-2 RECEPTOR AGONIST LIGANDS FOR TREATMENT OF ANGELMAN SYNDROME AND AUTISM

(71) Applicant: New York University, New York, NY (US)

(72) Inventors: Cristina Maria Alberini, New York, NY (US); Dirk Trauner, New York, NY (US); Christopher James Arp, The Woodlands, TX (US)

(73) Assignee: New York University, New York, NY (US)

( * ) Notice: Subject to any disclaimer, the term of this patent is extended or adjusted under 35 U.S.C. 154(b) by 641 days.

(21) Appl. No.: 17/267,715

(22) PCT Filed: Aug. 12, 2019

(86) PCT No.: PCT/US2019/046227
§ 371 (c)(1),
(2) Date: Feb. 10, 2021

(87) PCT Pub. No.: WO2020/033971
PCT Pub. Date: Feb. 13, 2020

(65) Prior Publication Data
US 2021/0315914 A1 Oct. 14, 2021

Related U.S. Application Data

(60) Provisional application No. 62/717,372, filed on Aug. 10, 2018.

(51) Int. Cl.
*A61K 31/7024* (2006.01)
*A61K 38/30* (2006.01)
*A61P 25/00* (2006.01)

(52) U.S. Cl.
CPC .......... *A61K 31/7024* (2013.01); *A61K 38/30* (2013.01); *A61P 25/00* (2018.01)

(58) Field of Classification Search
CPC . A61K 31/70; A61K 31/7012; A61K 31/7024
USPC ........................................................ 514/23
See application file for complete search history.

(56) References Cited

U.S. PATENT DOCUMENTS

| | | | |
|---|---|---|---|
| 6,093,388 A | 7/2000 | Ferguson | |
| 6,140,307 A | 10/2000 | Ferguson et al. | |
| 6,294,521 B1 | 9/2001 | Cowden | |
| 8,293,875 B2 | 10/2012 | Hassan et al. | |
| 8,551,960 B2 | 10/2013 | Montero et al. | |
| 2005/0256059 A1 | 11/2005 | Benowitz | |
| 2010/0081613 A1 | 4/2010 | Arancio et al. | |
| 2012/0009245 A1 | 1/2012 | Bankiewicz | |
| 2012/0045455 A1 | 2/2012 | Robertson et al. | |
| 2012/0093795 A1 | 4/2012 | Garcia et al. | |
| 2012/0266263 A1 | 10/2012 | Alberini et al. | |
| 2014/0056867 A1 | 2/2014 | LeBowitz et al. | |
| 2014/0187430 A1 | 7/2014 | Hu et al. | |
| 2015/0224164 A1 | 8/2015 | Glass et al. | |
| 2021/0322451 A1 | 10/2021 | Alberini et al. | |

FOREIGN PATENT DOCUMENTS

| | | |
|---|---|---|
| CN | 1660125 A | 8/2005 |
| TW | 200833711 A | 8/2008 |
| WO | 90/01938 A1 | 3/1990 |
| WO | 2011000958 A1 | 1/2011 |
| WO | 2011/033305 A1 | 3/2011 |
| WO | 2013119964 A2 | 8/2013 |
| WO | 2014085480 A1 | 6/2014 |

OTHER PUBLICATIONS

Montero et al, ChemMedChem Communications, 2011, 6(10), 1771-1774.*
Barragan-Montero et al, ChemMed Chem, 2011, 6, 1771-1774.*
Vidal et al, Bioorganic & Medicinal Chemistry, 2002, 10, 4051-4056.*
Steinmetz, A.B., et al., Insulin-Like Growth Factor II Targets the mTOR Pathway to Reverse Autism-Like Phenotypes in Mice, The Journal of Neuroscience, Jan. 24, 2018, vol. 38, No. 4, pp. 1015-1029.
Pubchem-CID: 67160412, 2-[(2R,3S,4S,5S)-3,4,5-Trihydroxy-6-methoxyoxan-2-yl]ethylphosphonic acid, Nov. 30, 2012, pp. 1-7.
Wang, Y., et al., Insulin-Like Growth Factor-II/Cation-Independent Mannose 6-Phosphate Receptor in Neurodegenerative Diseases, Molecular Neurobiology, Mar. 19, 2016, vol. 54, pp. 2636-2658. Mar. 19, 2016.
Jeanjean, A., et al., Synthesis and receptor binding affinity of carboxylate analogues of the mannose 6-phosphate recognition marker, Bioorganic & Medicinal Chemistry, 2006, vol. 14, pp. 3575-3582. 2006.
Ren, W., et al., Peripheral Nerve Injury Leads to Working Memory Deficits and Dysfunction of the Hippocampus by Upregulation of TNF-alpha in Rodents, Neuropsychopharmacology, Feb. 2, 2011, vol. 36, pp. 979-992. Feb. 2, 2011.
Stern, S.A., et al., "Systemic IGF-II treatment enhances memories and rescues autistic phenotypes", Society for Neuroscience, Nov. 11, 2013, 2 pages. https://www.abstractsonline.com/Plan/ViewAbstract.aspx?sKey=88150564-db5c-4893-b504-deff6dc69a03&cKey=ada4cf15-dde0-4731-acf6-ec9f19a24437&mKey=8d2a5bec-4825-4cd6-9439-b42bb151d1cf.
Stern, S.A., et al., "Memory enhancing effects of IGF-II and its role in social interaction in a mouse model of autism", Society for Neuroscience, Oct. 14, 2012, 3 pages. https://www.abstractsonline.com/Plan/ViewAbstract.aspx?sKey=89ffd578-bb38-41f7-8f92-3192b9ca5d54&cKey=98bf9e1c-d6b8-4d96-8293-4e6ec6cf4f83&mKey=70007181-01c9-4de9-a0a2-eebfa14cd9f1.

(Continued)

*Primary Examiner* — Ganapathy Krishnan
(74) *Attorney, Agent, or Firm* — Hodgson Russ LLP (57) ABSTRACT

Provided are methods for treatment of neurodevelopmental disorders, such as Angelman Syndrome and autism comprising administering to an individual a composition comprising an agonist ligand of IGF-2 receptor. The agonist ligand of IGF-2 receptor may be IGF-2, or mannose-6-phosphate or a derivative thereof. Compositions comprising mannose-6-phosphate derivatives are also disclosed.

4 Claims, 6 Drawing Sheets

(56) References Cited

OTHER PUBLICATIONS

Barragan-Montero, V. et al., "Synthesis of Mannose-6-Phosphate Analogues and their Utility as Angiogenesis Regulators", ChemMedChem Communications, Jul. 26, 2011, vol. 6, No. 10, pp. 1771-1774.

Clavel, C., et al., "Synthesis and biological activity of M6-P and M6-P analogs on fibroblast and keratinocyte proliferation", IL Farmaco, Sep. 2005, vo.. 60, No. 9, pp. 721-725.

Vidal, S., et al., "Synthesis and biological evaluation of new mannose 6-phosphate analogues", Bioorganic & Medicinal Chemistry, Dec. 2002, vol. 10, Issue 12, pp. 4051-4056.

Sun, J., et al., "mTORC1-S6K1 inhibition or mTORC2 activation improves hippocampal synaptic plasticity and learning in Angelman syndrome mice", Cellular and Molecular Life Sciences, May 12, 2016, vol. 73, pp. 4303-4314.

Gary-Bobo, M., et al. Mannose 6-Phosphate Receptor Targeting and its Applications in Human Diseases, Current Medicinal Chemistry, 2007, vol. 14, No. 28, pp. 2945-2953.

Cruz, E., et al. CIM6P/IGF-2 Receptor Ligands Reverse Deficits in Angelman Syndrome Model Mice, Autism Research, Jan. 2021, vol. 14, No. 1, pp. 29-45.

Sun, M., et al., Interactions between the recombinant human CREG protein and cathepsins and M6P/IGFIIR, Chinese Journal of Tissue Engineering Research, Sep. 10, 2015, vol. 19, No. 37, pp. 5961-5965.

Qiu et al., "Imprinted Angel—Angelman syndrome and Ube3a gene," The Mystery of the Brain, Aug. 31, 2017, pp. 131-136.

Lina et al., "Analysis of genomic copy number variation in 55 children with mental retardation/developmental delay using microarray comparative genomic hybridization," The Chinese Journal of Child Health Care, Aug. 31, 2014, pp. 795-798, vol. 22, Issue 8.

Murphy et al., "Imprinted Genes as Potential Genetic and Epigenetic Toxicologic Targets," Environmental Health Perspectives, Mar. 1, 2000, vol. 108, Supplement 1.

* cited by examiner

USE OF IGF-2 RECEPTOR AGONIST LIGANDS FOR TREATMENT OF ANGELMAN SYNDROME AND AUTISM

CROSS REFERENCE TO RELATED APPLICATIONS

This application claims priority to U.S. Provisional application No. 62/717,372, filed on Aug. 10, 2018, the disclosure of which is incorporated herein by reference.

STATEMENT REGARDING FEDERALLY SPONSORED RESEARCH OR DEVELOPMENT

This invention was made with government support under grant numbers MH065635 and MH074736 awarded by the National Institutes of Health. The government has certain rights in the invention.

BACKGROUND OF THE INVENTION

Angelman Syndrome (AS) is a neurological disorder that occurs in one in about 20,000 live births. Characteristics or symptoms of AS include developmental delay, lack of speech, walking and balance disorders, and seizures. Epileptic seizures may be of many types and are often non-responsive to many prescribed medications. AS is also associated with cognitive impairments. Some of the characteristics of Angelman Syndrome overlap with autism spectrum disorders, although the two conditions have their own unique characteristics. Currently, there is no known cure for AS or autism or no viable therapeutic approaches to ameliorate the various symptoms associated with these indications.

SUMMARY OF THE DISCLOSURE

The present disclosure provides methods for treatment of neurodevelopmental disorders, such as Angelman Syndrome (AS) and autism. The method comprises administering to a subject in need of treatment, a composition comprising an insulin-like growth factor 2 (IGF-2 or IGF-II) receptor agonist ligand, which is specific for the IGF-2 receptor. For example, the compositions may comprise, or consist essentially of, a therapeutically effect amount of IGF-2 and/or Mannose-6-phosphate (M6P), or derivatives thereof. Any derivative of M6P or IGF-2 that binds specifically to IGF-2 receptor may be used. Derivatives of M6P include, but are not limited to derivatives where carbon 1 is functionalized with an alkoxy group (e.g., methoxy, ethoxy, and the like) or an alkyne and carbon 6 is functionalized with a phosphonate, an ethyl ester, a methyl malonate, a phosphonic acid, a carboxylate, or a malonate.

BRIEF DESCRIPTION OF THE FIGURES

FIG. 1. IGF-2 reverses most behavioral deficits observed in a mouse model of AS. Experimental timelines are shown above graphs. In all experiments mice received a s.c. injection of either vehicle or IGF-2 (↑) 20 min before either training or testing. All data are expressed as the mean±s.e.m. N=8-12 per group. Two-way analysis of variance (ANOVA) followed by Bonferroni post-hoc tests. *$P<0.05$, $P<0.01$, *$P<0.001$. (A) Percentage of time spent freezing before (Pre-US) or after (Post-US) the shock delivery during contextual fear conditioning training and at testing at 24 hours (h) after training (Test) of normal mice (wild type, WT), which served as controls and Ube3a−/+ mice (mouse model of AS, also referred to as mice) injected with vehicle or IGF-2. (B) Percent exploration preference for a novel object compared to a familiar object during novel object recognition of WT and Ube3a−/+ mice injected with vehicle or IGF-2, 20 min before training, tested at 4 h and 24 h after training. (C) Percent of correct alternations (% Correct) in a Y-maze of WT and Ube3a−/+ mice injected with vehicle or IGF-2 before testing (Test). (D) Latency to fall off from a rotating rod by WT and Ube3a−/+ mice injected with vehicle or IGF-2, 20 min before Test, and tested again 3 and 7 days later. (E) Time spent burying marbles by WT and Ube3a−/+ mice injected with vehicle or IGF-2, 20 min before Test. (F) Time spent in the center of an open field by WT and Ube3a−/+ mice following a vehicle or IGF-2 injection given 20 min before Test. The bars for each set from left to right are: WT Vehicle, WT IGF-2, Ube3a−/+ Vehicle, and Ube3a−/+ IGF-2.

FIG. 2. Biochemical marker characterization of dorsal hippocampus (dHC) in AS mice compared to WT littermates. Western blot analyses of whole hippocampal protein extracts collected from untrained (referred to as naïve) 8 week-old Ube3a−/+mice and WT littermates. Each relative value was normalized against β-actin detected on the same blot (used as loading control). All data are expressed as the mean±s.e.m. and normalized to the mean value of WT naive mice. N=4 per group. Independent t-tests. *$P<0.05$, **$P<0.01$.

FIG. 3. Biochemical marker characterization of medial prefrontal cortex (mPFC) in AS mice compared to WT littermates. Western blot analyses of whole hippocampal protein extracts collected from the mPFC of naïve (untrained controls) 8 week-old Ube3a−/+ mice and WT littermates. Each relative value was normalized against β-actin detected on the same blot, which was used as loading control. All data are expressed as the mean±s.e.m. and normalized to the mean value of WT naive mice. N=4 per group. Independent t-tests. *$P<0.05$, **$P<0.01$.

FIG. 4. Dose-response curve of the effect of IGF2R.L1 (L1) (M6P) on nOR in normal (wild type, WT) mice. Experimental timeline is shown above graphs. Data are expressed as the mean±s.e.m. N=4 per group. One-way analysis of variance (ANOVA) followed by Bonferroni post-hoc tests. *$P<0.05$, **$P<0.01$. WT mice were injected s.c. with different doses of IGF2R.L1 (L1) 20 min prior to training on nOR. Graphs show percent exploration preference for the novel object compared to the familiar object at testing performed at 4 h and 24 h after training.

FIG. 5. M6P reverses cognitive and motor deficits in AS mice. Experimental timelines are shown above graphs. In all experiments mice received a s.c. injection of either vehicle or 850 μg/Kg of M6P (IGF-2R.L1 or L1)(↑) 20 min before either training or testing. (A) Percent exploration preference for a novel object compared to a familiar object during the nOR paradigm of WT (Control) and Ube3a−/+(AS) mice injected with vehicle or IGF-2R.L1 20 min before training, and tested at 4 h and 24 h after training. N=4/group. Data are expressed as the mean±s.e.m. Two-way analysis of variance (ANOVA) followed by Bonferroni post-hoc tests. *$P<0.05$, $P<0.01$, *$P<0.001$. (B) Percent of correct alternations (% Correct) in a Y-maze of WT and AS mice injected with vehicle or M6P before testing (Test). Data are expressed as the mean (±s.e.m.). (C) Hindlimb clasping scores of WT and AS mice injected with vehicle or IGF-2R.L1, 20 min before Test. Hindlimb clasping scores are measured and expressed as following: If the hindlimbs are consistently splayed outward, away from the abdomen, it is assigned a score of 0. If one hindlimb is retracted toward the abdomen for more than 50% of the time suspended, it receives a score of 1. If both hindlimbs are partially retracted toward the abdomen for more than 50% of the time suspended, it receives a score of 2. If its hindlimbs are entirely retracted and touching the abdomen for more than 50% of the time suspended, it receives a score of 3. Data are expressed in scores. B and C: N=8-14 per group. Two-way analysis of variance (ANOVA) followed by Tukey post-hoc tests. *P<0.05, P<0.01, *P<0.001.

FIG. 6. PnM6P reverses memory and motor deficits in AS mice. Experimental timelines are shown above graphs. In all experiments mice received a s.c. injection of either vehicle or 850 µg/Kg of phosphonate-M6P (PnM6P) called IGF-2R.L2 (or L2) (↑) 20 min before either training or testing. (A) Percent exploration preference for a novel object compared to a familiar object during the nOR paradigm of WT (Control) and Ube3a−/+ (AS) mice injected with vehicle or L2 before training, and tested at 4 h, 24 h and 5 days (5 d) after training. N=4/group. Data are expressed as the % mean±s.e.m. (B). Latency to fall off from a rotating rod by WT (Control) and AS mice injected with vehicle or L2, 20 min before Test (Test1), and tested again two days later (Test2). Data are expressed in seconds (s). (C) Hindlimb clasping scores of WT and AS mice injected with vehicle or L2 before Test. B and C: N=3-4 per group. Data are expressed in hindlimb scores. Two-way analysis of variance (ANOVA) followed by Bonferroni post-hoc tests. *P<0.05, P<0.01, *P<0.001.

DESCRIPTION OF THE DISCLOSURE

This disclosure provides compositions and methods for treatment of neurodegenerative disorders, such as Angelman Syndrome (AS) and autism spectrum disorder (ASD). The compositions and methods relate to IGF-2 receptor ligands.

The term "treatment" as used herein refers to reduction or delay in one or more symptoms or features associated with the presence of the particular condition being treated, e.g., Angelman syndrome. Treatment does not mean complete cure. For example, treatment of AS in the present disclosure means reducing or inhibiting one or more symptoms associated with AS.

The term "therapeutically effective amount" as used herein is the amount sufficient to achieve, in a single or multiple doses, the intended purpose of treatment. For example, an effective amount to treat AS is an amount sufficient to alleviate one or more symptoms of AS. The symptoms that are alleviated with the treatment may include one or more of developmental milestones, speech, intellectual abilities, movement (walking and balancing) social behavior and epilepsy. The exact amount desired or required will vary depending on the mode of administration, patient specifics and the like. Appropriate effective amounts can be determined by one of ordinary skill in the art (such as a clinician) with the benefit of the present disclosure.

Where a range of values is provided in this disclosure, it should be understood that each intervening value, to the tenth of the unit of the lower limit between the upper and lower limit of that range, and any other intervening value in that stated range is encompassed within the invention, unless clearly indicated otherwise. The upper and lower limits of these smaller ranges may independently be included in the smaller ranges encompassed within the disclosure.

As used in this disclosure, the singular forms include the plural forms and vice versa unless the context clearly indicates otherwise.

This disclosure describes the effects of agonist ligands of IGF-2 receptor on neurodevelopmental disorders like Angelman Syndrome (AS). In one aspect, this disclosure provides a method of treatment of a neurodevelopmental disorder such as Angelman syndrome or autism by administering to a subject in need of treatment, a composition comprising one or more agonist ligands of IGF-2 receptor. In this disclosure, the terms "individual" and "subject" may be used interchangeably. The subject may be any animal subject, such as a human, a laboratory animal, or any other animal. In one embodiment, the agonist ligand of the IGF-2 receptor is specific for the IGF-2 receptor and is not a ligand for IGF-2-related other receptors (such as IGF-1 or insulin receptors). For example, the agonist ligand (also referred to herein as agent) can be a modified mannose (such as, for example, M6P), a modified M6P (e.g., a derivative of M6P), IGF-2, or a modified IGF-2 or any chemical or peptide that binds to the IGF-2 receptor and activates its cellular response. Phosphonate and sulfonate derivatives of M6P are known in the art (U.S. Pat. No. 6,140,307 to Ferguson, the description of which modifications is incorporated herein by reference). Further, IGF-2 with amino acid substitutions such as human Leu 27 (Armitaj et al., Neuroscience, 2010 Oct. 27; 170(3):722-30) may also be used.

Modifications to M6P (also referred to herein as M6P derivatives) include modifications to carbon 1 and/or carbon 6 of mannose. Examples of derivatives include examples where carbon 1 is functionalized with an alkoxy group (e.g., methoxy, ethoxy, and the like) or an alkyne and carbon 6 is functionalized with a phosphonate, an ethyl ester, a methyl malonate, a phosphonic acid, a carboxylate, or a malonate. In various examples, carbon 1 is functionalized with an alkoxy (e.g., a methoxy) and carbon 6 is functionalized with a phosphonate (referred to herein as L2), an ethyl ester (referred to herein as L3), a methyl malonate (referred to herein as L4), a phosphonic acid (referred to herein as L5), a carboxylate (e.g., the sodium salt of a carboxylate) (referred to herein as L6), or a malonate (referred to herein as L7) and carbon 1 is functionalized with alkyne and carbon 6 is functionalized with a phosphonic acid (referred to as L8) or a phosphonate (referred to as L9). The structures for M6P and its derivatives listed above are shown below:

L1

L2

The agonist ligand may bind to the IGF-2 receptor with an affinity similar to that of IGF-2 or M6P. It is known that IGF-2 binds to its receptor with a $K_d$ of about 40-60 nM (Williams et al., Science, 2012 Nov. 30, 338(6111):1209-1213) and M6P binds to the IGF-2 receptor with an affinity that may be about 1 nM or about 1 μM (depending upon which of the two known sites it binds to) (Olson et al., J. Biol., Chem. 2004 Aug. 6; 279(32):34000-9. Epub 2004 May 28).

Generally, a therapeutic dose of IGF-2 receptor ligand for the present disclosure is in the range of about 1 to 10,000 microgram/kg body weight. IGF-2 may be used at from about 1 to 500 μg/kg body weight and all values and ranges therebetween. For example, IGF-2 may be used at 1 to 500 μg/kg, 1 to 100 μg/kg, 1 to 50 μg/kg, 10 to 500 μg/kg, 10 to 100 μg/kg, 10 to 50 μg/kg body weight. In one embodiment, IGF-2 can be used at 10 to 45 μg/kg administered subcutaneously. In specific embodiments, IGF-2 can be used at 10, 15, 20, 25, 30, 35, 40, 45, 50, 55, 60, 65, 70, 75, 80, 85, 90, 95, 100, 200, 300, 400 and 500 μg/kg body weight.

M6P and M6P derivatives may be used at from about 1 to 2,000 μg/kg body weight and all values and ranges therebetween. For example, M6P may be used at from 1 to 2,000 μg/kg, 1 to 1,500 μg/kg, 1 to 1,000 μg/kg, 1 to 500 μg/kg, 1 to 100 μg/kg, 10 to 2,000 μg/kg, 10 to 1,500 μg/kg 10 to 1,000 μg/kg, 10 to 500 μg/kg, 10 to 100 μg/kg, 50 to 2,000 μg/kg, 50 to 1,500 μg/kg, 50 to 1,000 μg/kg, 50 to 500 μg/kg, and 50 to 100 μg/kg body weight and all values between the aforementioned ranges. In an embodiment, M6P or derivatives can be used at 850 μg/kg administered subcutaneously. In an embodiment, M6P or derivatives can be used at 100 to 1,000 μg/kg. In specific embodiments, M6P can be used at 50, 100, 150, 200, 250, 300, 350, 400, 450, 500, 550, 600, 650, 700, 750, 800, 850, 900, 950, 1000, 1,250, 1,500, 1,750 and 2,000 μg/kg body weight. Further, based on the data provided herein on animals, one skilled in the art can obtain relevant human dosage for M6P and IGF-2. Guidance for such conversions is known in the art (See, for example, Nair et al., J. Basic Clin. Pharma., v 7(2), March 2016-May 2016; 27-31, incorporated herein by reference).

M6P may be present in the form of the free phosphoric acid or a pharmaceutically acceptable mono- or di-salt thereof, such as, for example as sodium, calcium, magnesium or barium salt. It may also be provided as a M6P containing compound from which it may be released in vivo, or it may be provided as a precursor from which it may be produced in vivo. M6P derivatives may also be present (where applicable (e.g., L3, L7, and L8)) as free acids or as salts thereof (e.g., monosodium or disodium salts thereof).

In an aspect, this disclosure provides a method for treatment of neurodevelopmental disorders characterized by developmental delays in speech and movement, intellectual disability, seizures by about toddler age, and unusual behaviors and/or repetitive behaviors such as hand flapping. Examples of such neurodevelopmental disorders include Angelman syndrome and autism spectrum disorders.

Angelman Syndrome is a neurogenetic disorder characterized by intellectual and developmental delay. AS is caused by mutation of the E3 ubiquitin ligase Ube3A. Symptoms of Angelman Syndrome can include: developmental delays such as a lack of crawling or babbling at 6 to 12 months, attenuated mental development, no or minimal speech, ataxia (inability to move, walk, or balance properly), stiff or jerky movements (e.g., hand-flapping), hyperactivity, trembling in the arms and legs, frequent smiling and laughter, bouts of inappropriate laughter, widely spaced teeth, a happy, excitable personality, epilepsy, an electroencephalographic abnormality with slowing and notched wave and spikes, seizures which usually begin at 2 to 3 years of age and may be accompanied by myoclonus and atypical absence, partial seizures with eye deviation and vomiting, a small head which is noticeably flat in the back (microbrachyoephaly), crossed eyes (strabismus), thrusting of the tongue and suck/swallowing disorders, protruding tongue, excessive chewing/mouthing behaviors, hyperactive lower extremity deep tendon reflexes, wide-based gait with pronated or valgus-positioned ankles, increased sensitivity to heat, walking with the arms up in the air, fascination with water or crinkly items such as some papers or plastics, obesity in older children, constipation, a jutting lower jaw, light pigmentation of the hair, skin, and eyes (hypopigmentation), frequent drooling, prognathia, feeding problems and/or truncal hypotonia during infancy, and/or scoliosis. Symptoms are usually not evident at birth and are often first evident as developmental delays such as a failure to crawl or babble between the ages of 6 to 12 months as well as slowing head growth before the age of 12 months. Individuals with Angelman Syndrome may also suffer from sleep disturbances including difficulty initiating and maintaining sleep, prolonged sleep latency, prolonged wakefulness after sleep onset, high number of night awakenings and reduced total sleep time, enuresis, bruxism, sleep terrors, somnambulism, nocturnal hyperkinesia, and snoring.

Severity of symptoms for AS can be measured clinically (Williams et al., American Journal of Medical Genetics 2005 140A; 413-8, incorporated herein by reference) and quantification of the severity of different symptoms can also be carried out (Lossie et al., Journal of Medical Genetics 2001, 38; 834-845, incorporated herein by reference; Ohtsuka et al., Brain and Development 2005, 27; 95-100, incorporated herein by reference). This may include the extent of language ability, degree of independent mobility, frequency and severity of seizures, ability to comprehend language, acquisition of motor skills, growth parameters. A screening procedure for suspected Angelman syndrome patients that quantifies the severity of 22 distinct criteria (Lossie et al., Journal of Medical Genetics 2001, 38) can be used. Other measurements of AS severity include psychometric methods to distinguish the degree of developmental delay with respect to psychomotor developmental achievement, visual skills, social interactions based on non-verbal events, expressive language abilities, receptive language abilities, and speech impairment. The degree of gait and movement disturbances as well as attention ability and the extent of EEG abnormalities can be measured (Williams et al., American Journal of Medical Genetics 2005 140A; 413-8). At appropriate age intellectual ability tests can also be used, such as the Kaufman Brief Intelligence Test-2 (KBIT-2; Kaufman & Kaufman, Circle Pines, MN: American Guidance Services; 2004, incorporated herein by reference). One or more of the above characteristics can be used to evaluate the effectiveness of treatment with the present compositions.

In an embodiment, assessment protocols to evaluate the effect of treatment include neurological and neurovisual examination and the evaluation of motor (e.g. Gross Motor Function Measure Scale), cognitive (e.g. Griffiths Mental Development Scale and Uzgiris-Hunt Scale and spatial working memory tests); adaptive (e.g. Vineland Adaptive Behavioral Scale); communication (e.g. MacArthur-Bates Communicative Development Inventory and video-recordings children's verbal expression), behavioral aspects (e.g. IPDDAG Scale) and neurovisual aspects as described in Micheletti et al., (Ital J Pediatr. 2016; 42(1): 91), incorporated herein by reference.

Autism spectrum disorders (ASD) are characterized by complex developmental disability that interferes with the normal development of the brain, particularly impacting social interaction and communication skills. It typically appears during the first three years of life. Autistic individuals have difficulties in verbal and non-verbal communication, social interactions, and leisure or play activities. Impairment in social interaction range from difficulty initiating and maintaining interaction, impaired ability to recognize and experience emotions, and difficulty processing and appreciating the feelings of others. Communication deficits vary amongst autistic individuals, with some autistic individuals having severely limited form of communication to individuals having significant language skills. Repetitive and stereotypic behaviors include complex rituals, difficulty in adapting to change, and unusual movements such as hand flapping. Some characteristic behavior which may be useful for diagnosing autism includes lack of or delay in spoken language, repetitive use of language or motor mannerisms (hand flapping or twirling objects), little or no eye contact, persistent fixation on certain objects, and lack of interest in socializing.

Administration of IGF-2, IGF-2 modifications (e.g., IGF-2 analogs), M6P or its derivatives can be initiated as soon as the diagnosis is made. The frequency and length of treatment can be determined by monitoring one or more symptoms of AS or ASD. The treatment can be continued as long as needed, including days, months, or years. The treatment can be continued even after the symptoms have subsided or no longer measurable.

The agents of the present disclosure can be provided in pharmaceutical compositions for administration by combining them with any suitable pharmaceutically acceptable carriers, excipients and/or stabilizers. Examples of pharmaceutically acceptable carriers, excipients and stabilizer can be found in *Remington: The Science and Practice of Pharmacy* (2005) 21st Edition, Philadelphia, PA. Lippincott Williams & Wilkins. For example, M6P can be used as a suspension or solution. Suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol;

resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may contain from 0.01 to 99% weight per volume or weight per weight of the active material (e.g., M6P or derivative thereof or IGF-2 or modification (e.g., IGF-2 analogs) thereof).

Administration of present compositions, can be carried out using any suitable route of administration known in the art. For example, the compositions may be administered via intravenous, intramuscular, intraperitoneal, intracerebrospinal, subcutaneous, intra-articular, intrasynovial, oral, topical, or inhalation routes. The compositions may be administered parenterally or enterically. In one embodiment, the compositions of the present disclosure can be administered orally, such as, for example, in the form of a tablet, capsule, pill, powder, paste, granules, elixir, solution, suspension, dispersion, gel, syrup or any other ingestible form. The M6P and/or derivatives thereof and/or IGF-2 and/or modifications (e.g., IGF-2 analogs) thereof may be delivered via liposomes, microparticles, microcapsules. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

In an embodiment, the IGF-2 receptor ligand is the only active component. By active component is meant that it is the only component in the composition that specifically binds to IGF-2 receptor. The IGF-2 receptor ligand can be IGF-2, modifications (e.g., IGF-2 analogs) thereof, or M6P or other M6P derivatives. In an embodiment, the M6P or its derivative is the only active component. In an embodiment, the M6P or its derivative is not linked (e.g., is not covalently bound either directly or via linker) to any other moiety and does not act as a carrier for any other moiety or agent. In an embodiment, the M6P derivative may be L2, L3, L4, L5, L6, L7, L8 or L9.

In an aspect, this disclosure provides M6P derivatives and compositions comprising mannose derivatives. Derivatives of M6P can be made by performing chemistry at carbon 1 and/or carbon 6 of M6P. Various methods of performing chemistry at carbon 1 and/or carbon 6 of hexoses are known in the art. Examples of M6P derivatives include, but are not limited to, phosphonate (L2), ethyl ester (L3), methyl malonate (L4), phosphonic acid (L5), carboxylate (L6), malonate (L7), alkyne (L8), and alkyne prodrug (L9). In an embodiment, this disclosure provides a compound selected from the group consisting of L2, L3, L4, L5, L6, L7, L8 and L9. In an embodiment, this disclosure provides a composition comprising one or more of L1, L2, L3, L4, L5, L6, L7, L8 and L9.

The following examples are provided as illustrative examples and are not intended to be restrictive in any way.

Example 1

Mouse Model Used:

The mice were obtained by breeding mutant male mice (B6.129S7-Ube3atm1Alb/J) carrying a paternally imprinted Ube3A (ubiquitin protein ligase E3A) knockout mutation (ordered from Jackson labs www.jax.org; stock #016590), with C57BL/6J female normal mice. Female heterozygous mice were bred with male C57BL/6J mice; the progeny from this cross are heterozygous males (maternal transmission), heterozygous females (maternal transmission), wild type males, and wild type females. These progeny were used for behavioral and biochemical studies. These mice are referred to herein as mice and their normal littermates as wild type (WT) mice or control mice.

Treatment:

subcutaneous (s.c.) injection of IGF-2, or vehicle control solution, 20 minutes before starting behavioral procedures.

Results:

IGF-2 Reverses Impaired Memory and Motor Responses as Well as Repetitive Behaviors in an AS Mice.

Figure 1:
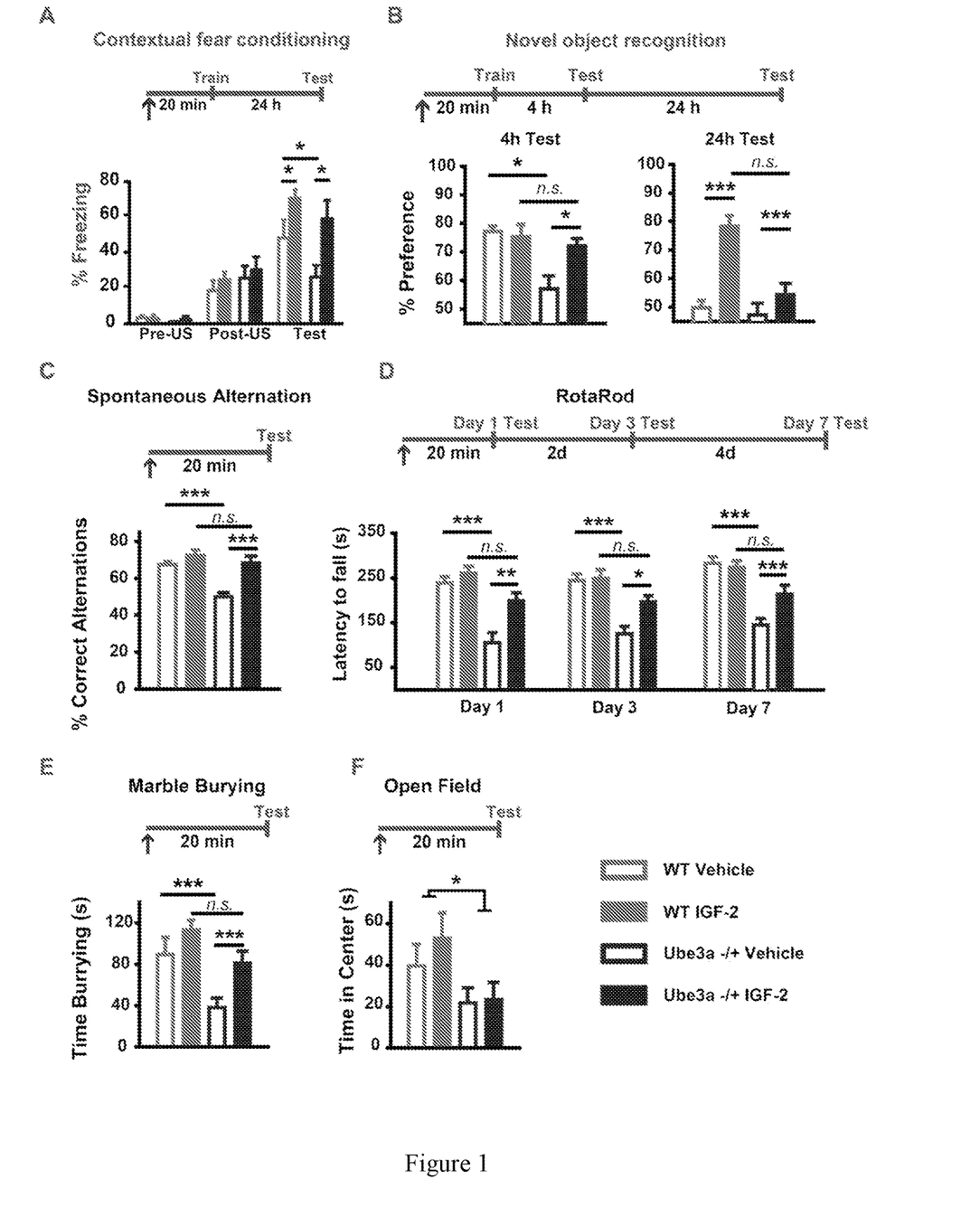

As measures of learning/cognitive responses, which are known to be altered in Angelman Syndrome (AS), we tested different types of aversive and non-aversive memories. We found that AS mice display a robust deficit in both aversive (contextual fear conditioning; CFC), and non-aversive (novel object recognition; nOR) forms of long-term memory. Specifically, in the CFC paradigm, mice were trained to associate a chamber (context) with an aversive foot shock. IGF-2 or vehicle solution was injected 20 minutes before training. We tested memory retention one day later (a time that is used to measure long-term memory) by placing mice back in the same chamber and measured their fear-related (freezing) behavior. We found that whereas WT littermate mice (controls) injected with control solution (vehicle) had a strong memory, evidenced by a robust freezing response, vehicle-injected AS mice showed significantly less freezing behavior, indicating a deficit in long-term memory retention (FIG. 1A). In contrast, AS mice treated with IGF-2 showed similar freezing, and therefore similar memory retention as control mice, indicating that IGF-2 completely reversed the memory impairment of AS mice.

We found similar outcomes with the non-aversive memory, nOR test. This task is a validated test for recognition memory, and it is based on the spontaneous tendency of rodents to spend more time exploring a novel object than a familiar one. Mice were exposed to two identical objects in a novel arena, and the time spent exploring each object was measured. Subsequently, 4 h and 24 h after the first experience, mice were returned to the same arena, but this time one of the objects was replaced by a novel object, and time spent exploring both objects was measured. When tested 4 h after training, as expected, control mice spent a significantly greater percent of time exploring the novel object, indicative of memory for the first object. In contrast, AS mice did not display such preference, and spend equal time exploring both objects, revealing memory impairment (FIG. 1B). IGF-2 injection completely reversed the memory deficits of AS mice as shown by their significant preference for the novel object. Moreover, although both control and AS mice showed a significant decay of memory retention when tested 24 h after training, both groups of mice treated with IGF-2 had a significant preference for a novel object, indicating that the ability of IGF-2 to reverse the long-term memory deficit observed in AS is persistent.

To assess exploratory strategies and working memory, we employed a spontaneous alternation paradigm using a three-arm Y-maze. We found that vehicle-injected control mice (WT) alternated their exploration between the three arms, whereas vehicle-injected AS mice alternated more between recently visited arms prior to exploring a non-visited arm, in a repetitive manner (FIG. 1C). In contrast, AS mice treated with IGF-2, 20 min prior to exposure to the Y-maze, had a similar exploratory strategy as control mice, indicating that IGF-2 reverses the repetitive, inflexible behavior seen in these mice.

AS is also associated with robust motor impairments, which again are reproduced in the AS mice. Motor coordination and ability is reliably assessed in mice by placing them on an accelerating rotating rod (RotaRod test). In this test, we observed a robust deficit in motor ability in vehicle treated AS mice compared to WT control mice (FIG. 1D). However, AS treated with IGF-2 showed a significant improvement in motor ability on the RotaRod, and in fact their falling latencies returned to similar levels as those of normal control mice.

We also observed a significant difference in the behavior displayed by AS mice compared to control WT littermates in the marble-burying test. When placed in an empty home cage with bedding and marbles, normal mice typically engage in a modest amount of burying behavior. In comparison to these control mice, AS mice showed extremely low levels of burying, exhibiting a significant reduction in both the time spent burying (FIG. 1E) and the amount of marbles buried. However, IGF-2 treatment rescued the deficits of the AS mice, which then showed similar levels of burying as normal mice.

To measure the effect of IGF-2 on anxiety-like behavior we employed open field and measured center entry (which measures anxiety behavior): No effect of IGF-2 treatment was found on AS mice, which remained altered compared to the behavior of normal mice (FIG. 1F).

Biochemical Characterization of Hippocampus and Medial Prefrontal Cortex in Basal Conditions Show Abnormalities in IGF-2 Pathway, Plasticity and Metabolism Markers.

We performed western blot analysis to compare the protein levels in two brain regions important for learning and memory and executive functions, the dorsal hippocampus (dHC) and the medial prefrontal cortex (mPFC) of adult AS mice and WT littermates under basal conditions (remained in the home cage). We found evidence of significant alterations in classes of markers critical for glucose metabolism, plasticity, inhibitory neurons function and IGF-2 pathways in the dorsal hippocampus (dHC) and medial prefrontal cortex (mPFC). Specifically, we assessed whole protein and synaptoneurosomal (synaptic fraction) extracts in AS and WT littermates to compare the expression levels of: i) IGF-2 and IGF-2R, ii) mTOR and phospho-mTOR, ULK-1 and phospho-ULK-1; iii) excitatory neuron plasticity (Arc/Arg3.1, GluA1, GluA2), iv) inhibitory neurons markers (GAD67), and v) glucose/energy metabolism (LDHB, MCT1, MCT4, MCT2, GLUT1, GLUT3, pAMPK).

Figure 2:
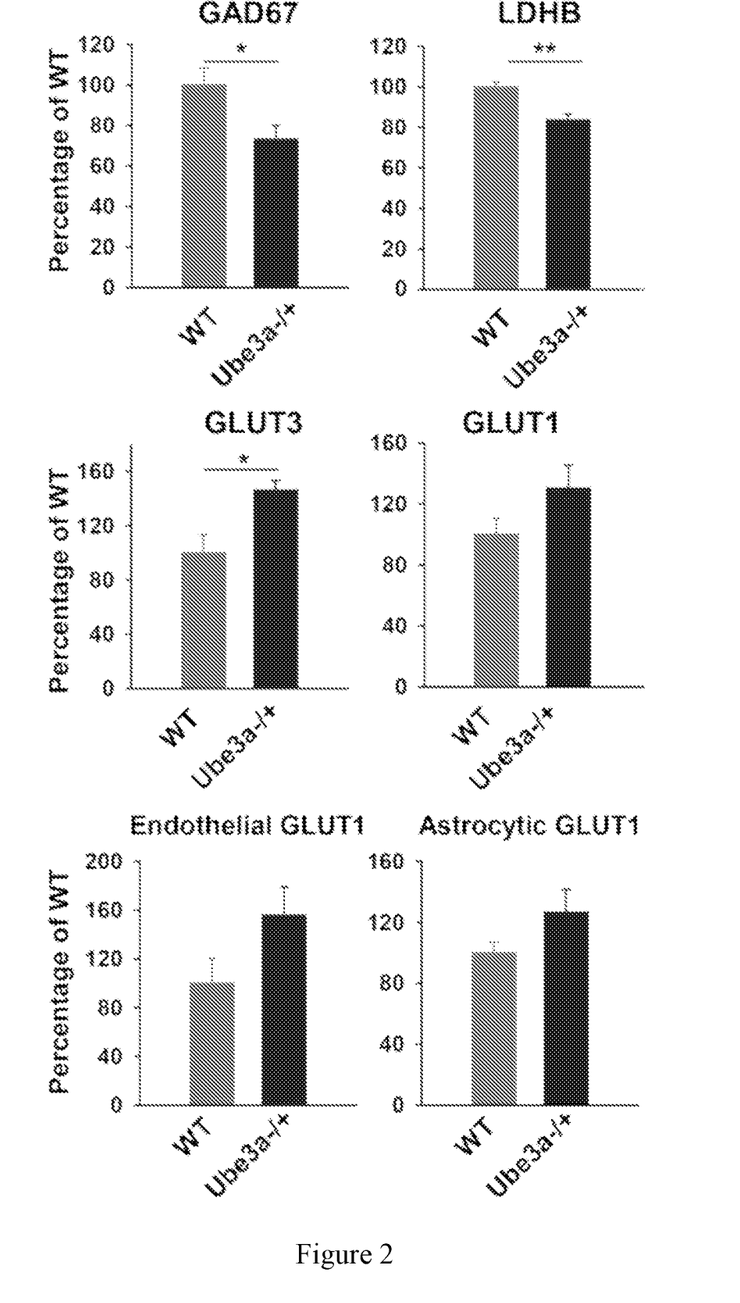
Figure 3:
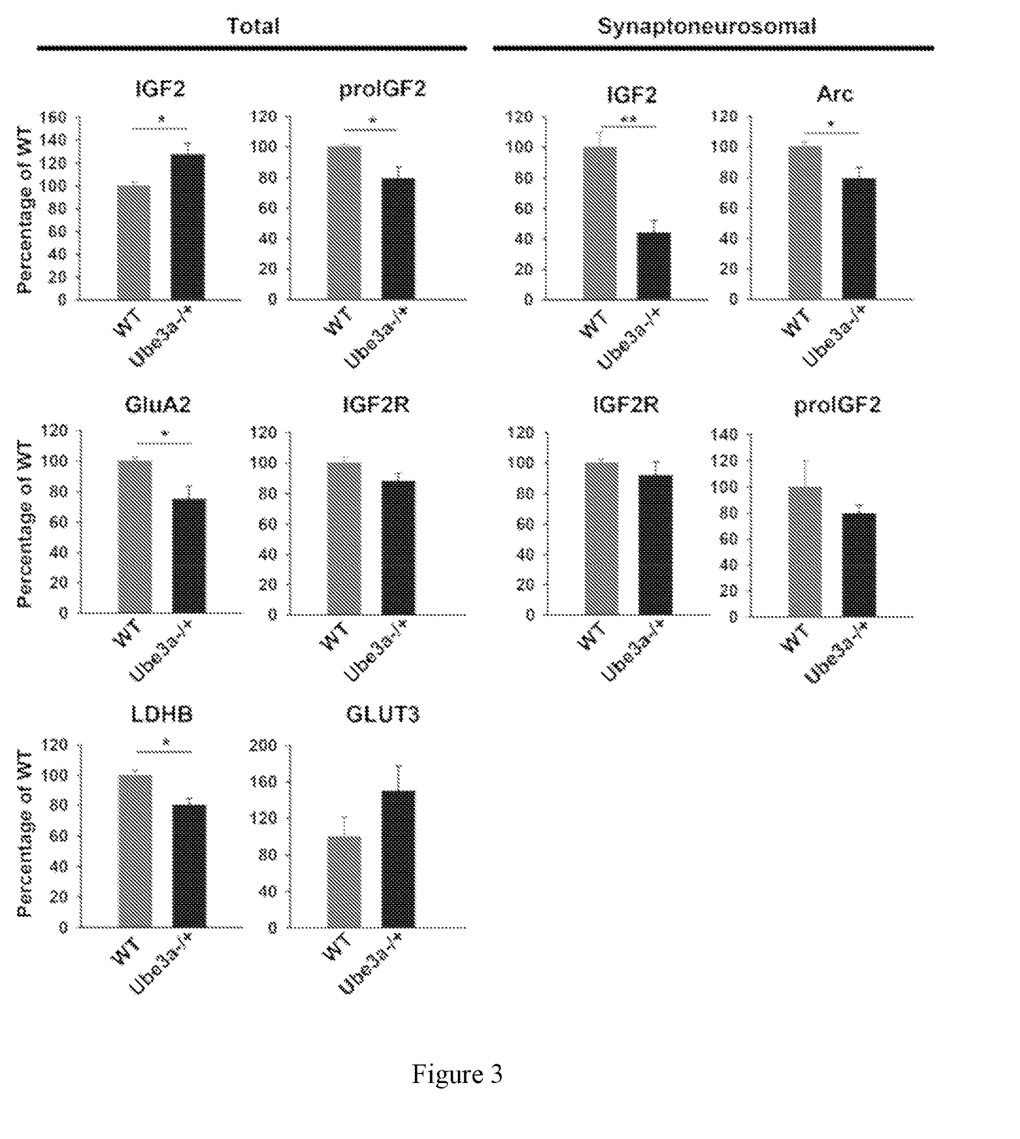

The analyses carried out thus far indicate that, compared to WT littermates, AS mice have alterations in IGF-2/IGF-2R, plasticity and glucose metabolism mechanisms in both brain regions. Specifically, as shown in FIGS. 2 (dHC) and 3 (mPFC), AS mice have a significant decrease in GAD67 in the dHC, suggesting alterations in inhibitory neurons. AS dHC also has a significant decrease in the metabolic enzyme lactate dehydrogenase B (LDHB) and a significant increase in GLUT3, as well as a strong trend of increased total, endothelial, and astrocytic GLUT1, suggesting that the glucose metabolism in AS mice is significantly altered. The AMPA receptor subunit, GluA2 showed a robust reduction trend, but it did not reach significant levels. Increasing the number of samples is likely to reveal a significant deficit. The levels of IGF-2, IGF-2 receptor, AMPA receptor subunit GluA1, plasticity related gene Arc/Arg3.1, synaptically enriched protein PSD95, pULK and the monocarboxylate transporters MCT1, MCT4, and MCT2 were unaltered under basal conditions in the dHC of AS mice.

In the mPFC (FIG. 3) there are more significant alterations in the IGF-2 pathway, with a significant increase of the mature form of IGF-2 and a significant decrease of pro-IGF-2 in the whole protein extract, whereas synaptoneurosomal fractions show a dramatic decrease of a mature form of IGF-2 and a strong trend towards reduction of pro-IGF-2 (immature form) in the AS mice compared to normal mice. IGF-2 receptor levels are not affected in the mPFC of AS mice. Synaptoneurosomal fractions also revealed a significant decrease of the immediate early, plasticity related gene, Arc/Arg 3.1, and there are also significant decreases in GluA2, but not in GluA1. Similarly to the dHC, significant decreased level of LDHB and a strong trend to a decrease in GLUT3 were found in the mPFC of AS mice. The levels of the neuronal inhibitory marker GAD67 were partially reduced in the mPFC, but it was not yet reaching statistically significant values. Moreover, pAMPK, PSD95, pULK monocarboxylate transporters MCT1, MCT4, and MCT2, levels were unaltered in the mPFC of AS mice.

Example 2

Figure 4:
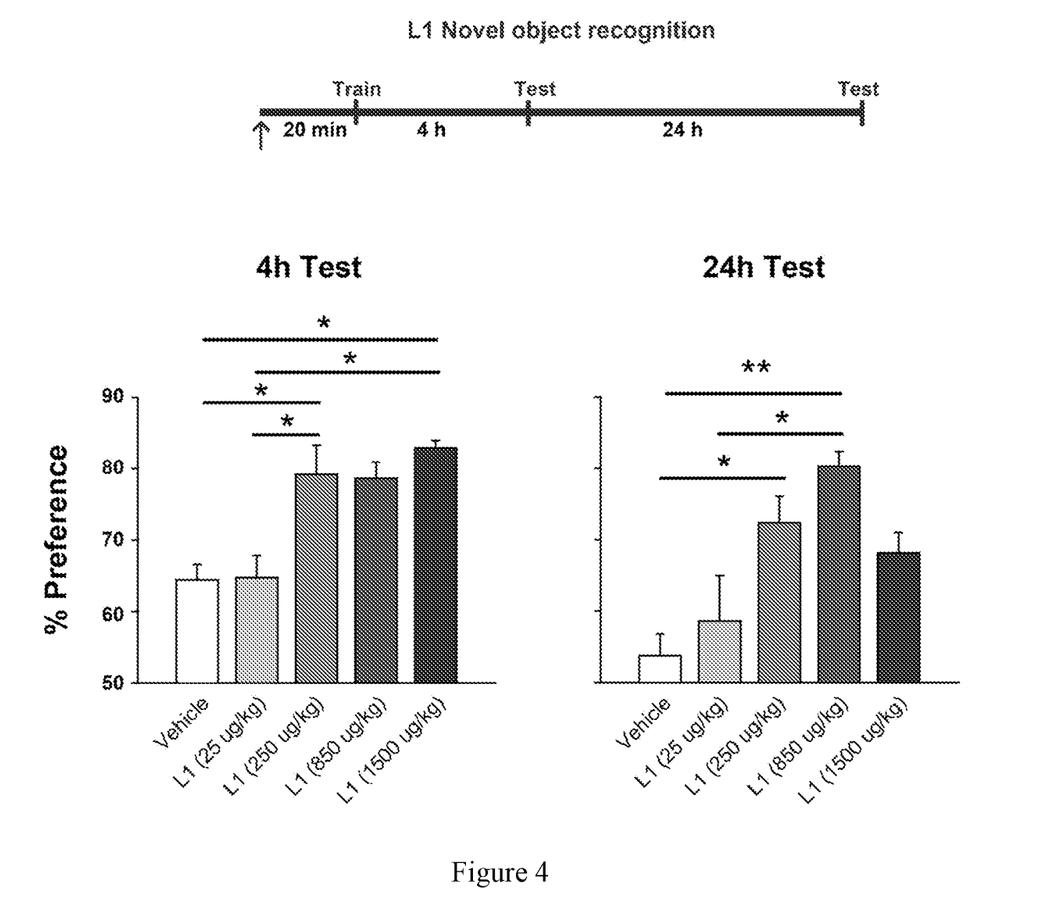

This example demonstrates that systemic administration of mannose-6-phosphate (M6P) reverses memory deficit in the Angelman syndrome mouse model. We first tested different M6P concentrations for effect on memory enhancement in normal mice. Results are shown in FIG. 4. IGF2R.L1 is M6P.

Figure 5:
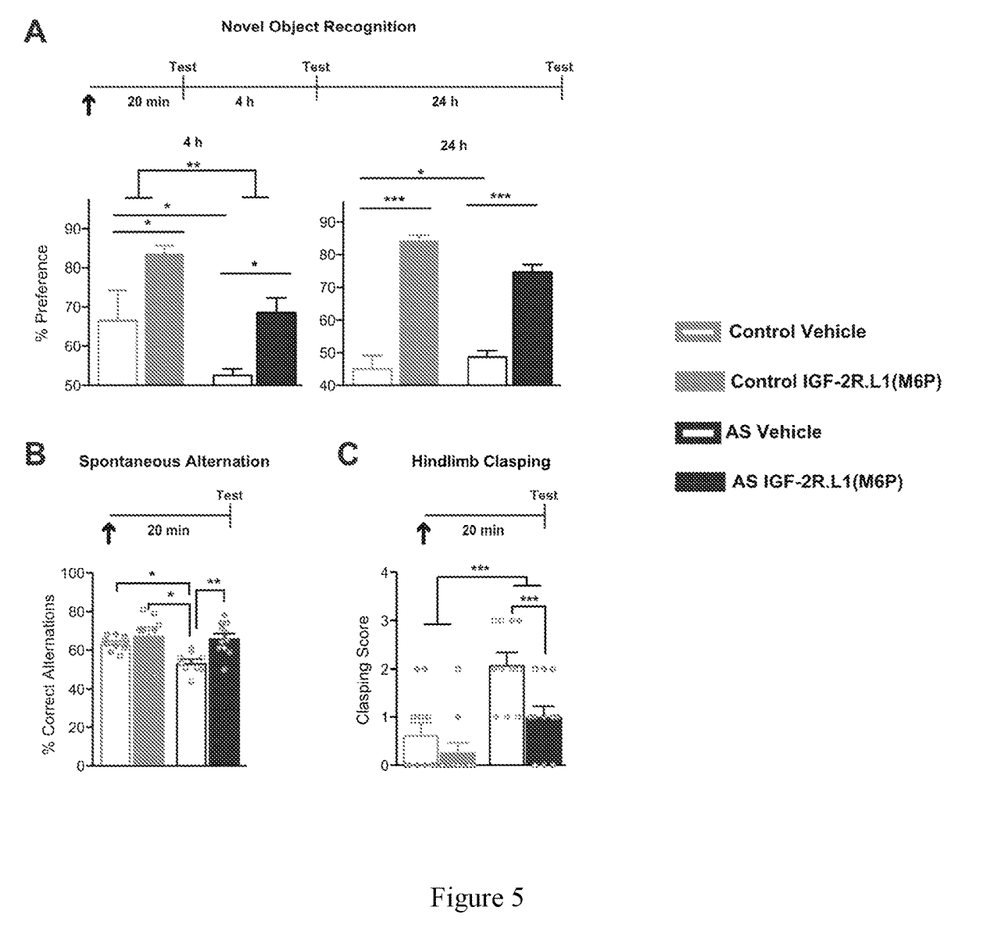

Further, we found M6P administered systemically in mice modeling Angelman syndrome (Ube3a−/+ mice, AS mice) reverses their memory impairments (FIG. 5).

Specifically, we used the novel object recognition (nOR) paradigm in mice to assess non-aversive episodic memory. In this task, the innate preference for novelty of the rodent is used. During training, the mouse is allowed to explore 2 identical objects. On test day, one of the training objects is replaced with a novel object. Because mice have an innate preference for novelty, if the mouse recognizes the familiar object, it will spend more time at the novel object.

A s.c. injection of M6P reversed memory impairment of AS mice. As depicted in FIG. 5A, testing at 4 h after nOR training revealed that, whereas control (wild type littermates, WT) mice injected with control solution (vehicle) had a strong memory, vehicle-injected AS mice showed significant memory impairments, confirming their established memory deficits. M6P injection prior to training reversed memory deficits in AS mice, which in fact had memory retention levels similar to those of control WT mice. When tested at 24 hours after training both WT and AS mice showed significant memory retention, whereas vehicle-injected WT and AS mice forgot (FIG. 5A).

As indicated above, AS mice show deficits in exploratory strategies/working memory, measured with a spontaneous alternation paradigm in a three-arm Y-maze. IGF-2R.L1 (M6P) injection, compared to vehicle injection, completely reversed the deficit (FIG. 5B).

AS is also associated with motor impairments, which are reproduced in the AS mice. One test used to assess motor problems is hind limb clasping, which is observed in mice models in which motor systems are impaired including in neurodegenerative diseases of the motor system. This test reveals paw-clasping and a bat-like posture in mice with motor deficits when suspended by the tail instead of a flexion response. As shown in FIG. 5C, vehicle-injected AS mice showed a significant hind-lib clasping response compared to WT control mice. IGF-2R.L1 injection in AS mice significantly reduced hind limb clasping, hence reversed their deficit.

Example 3

Figure 6:
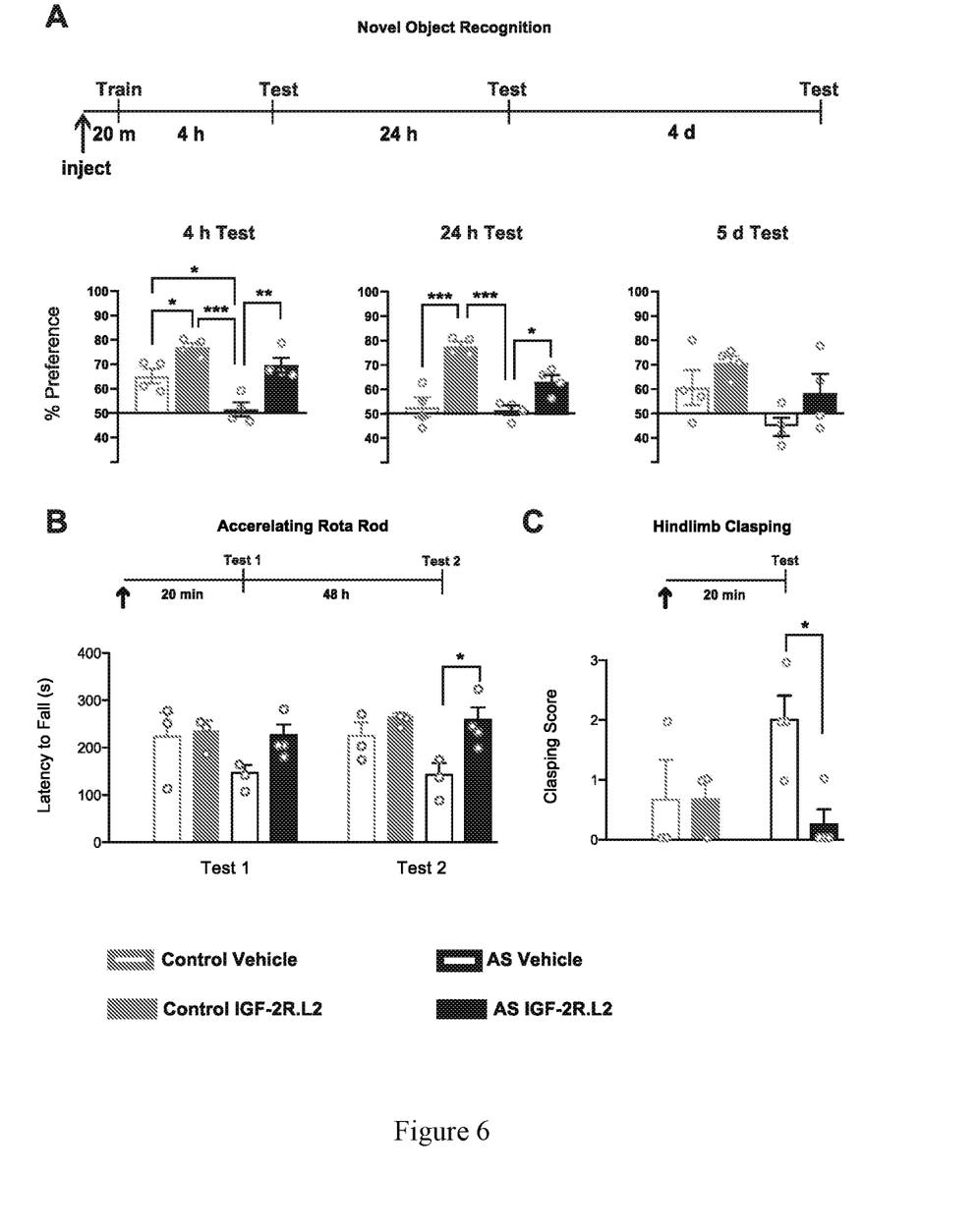

We tested a modified M6P: a phosphonate-M6P (PnM6P) called IGF-2R.L2 (or L2). As depicted in FIG. 6, L2, injected at 850 µg/kg, significantly reversed the deficit of AS mice in nOR and significantly enhanced nOR memory retention in WT mice at 4 hours after training (FIG. 6A). At 24 hours after training both WT and AS mice injected with L2 showed significant memory compared to vehicle-injected groups. When re-tested at 5 hours after training (5 d test) none of the groups (vehicle or L2 injected) showed significant memory, although WT controls displayed a strong tendency toward memory enhancement, which may become significant when a higher number of subjects per group will be included.

L2 also reversed motor deficits of AS mice as revealed by the RotaRod test (described in 0034). While vehicle-injected AS mice showed a significant deficit in motor ability compared to WT control mice (FIG. 6B), L2-injected AS mice significantly improved their motor ability on the RotaRod, and in fact their falling latencies returned to levels similar to those of WT control mice (FIG. 6B).

L2 injection reversed motor deficits as measured by hindlimb clasping. While vehicle-injected AS mice showed significantly high score of hindlimb clasping behavior compared to vehicle-injected control mice, L2-injected AS mice returned their hindlimb clasping behavior to control levels (FIG. 6C).

Example 4

This example describes the synthesis and characterization of M6P derivatives.

General Synthetic Procedures

All reactions were performed in flame-dried or oven-dried glassware under a positive pressure of nitrogen or argon with magnetic stirring, unless otherwise stated. Anhydrous dichloromethane ($CH_2Cl_2$), diethyl ether ($Et_2O$), 1,4-dioxane, tetrahydrofuran (THF), toluene (PhMe), and N,N-dimethylformamide (DMF) were obtained by passing the solvent through activated alumina columns into flame-dried glassware. Other solvents and reagents were used as obtained from commercial vendors (Acros Organics, AK Scientific, Alfa Aesar, Chem-Impex International, Combi-Blocks, Sigma-Aldrich, Strem Chemicals, Synthonix, Tokyo Chemical Industry Co.) unless otherwise described. Thin-layer chromatography (TLC) was performed for reaction monitoring using silica gel 60 glass plates pre-coated with $F_{254}$ fluorescent indicator (Millipore Sigma) and visualized by blocking of ultraviolet light ($\lambda$=254 nm) or by staining with aqueous potassium permanganate ($KMnO_4$) solution, aqueous acidic ceric ammonium molybdate (IV) (CAM) solution, acidic ethanolic p-anisaldehyde solution, or butanolic ninhydrin solution, followed by gentle heating with a heat gun. Flash-column chromatography was performed at room temperature under pressure of nitrogen with silica gel (60 Å, 40-63 µm, Silicycle or Merck) using glass columns or a Teledyne Isco MPLC CombiFlash® Rf+. Proton nuclear magnetic resonance ($^1$H NMR) spectra were recorded on a Bruker Avance III HD 400 MHz spectrometer equipped with a CryoProbe™ at 25° C., are reported in parts per million (ppm, δ scale) downfield from tetramethylsilane (TMS, δ=0 ppm), and are referenced internally to the residual protium resonances of the NMR solvent ($CDCl_3$: 7.26 [$CHCl_3$], $CD_3OD$: 4.87 [MeOH], $D_2O$: 3.31 [$H_2O$], $C_6D_6$: 7.16 [$C_6H_6$], $(CD_3)_2SO$: 2.50 [$(CH_3)_2SO$]). Proton-decoupled carbon-13 nuclear magnetic resonance ($^{13}C\{^1H\}$ NMR) spectra were recorded on a Bruker Avance III HD 400 MHz spectrometer equipped with a CryoProbe™ at 25° C., are reported in parts per million (ppm, δ scale) downfield from tetramethylsilane (TMS, δ=0 ppm), and are referenced internally to the central line of carbon-13 resonances of the NMR solvent ($CDCl_3$: 77.36 [$CHCl_3$], $CD_3OD$: 49.00 [MeOH], $(CD_3)_2SO$: 39.52 [$(CH_3)_2SO$]). Proton-decoupled phosphorus-31 nuclear magnetic resonance ($^{31}P\{^1H\}$ NMR) spectra were recorded on a Bruker Avance III HD 400 MHz spectrometer equipped with a CryoProbe™ at 25° C., are reported in parts per million (ppm, δ scale) downfield from phosphoric acid ($H_3PO_4$, δ=0), and are referenced externally to a triphenyl phosphate standard solution (0.0485 M in $CDCl_3$, δ=−17.7 ppm). The reported data are represented as: chemical shift in parts per million (ppm, δ scale) (integration, multiplicity, coupling constants J in Hz, atom assignment).

Multiplicities are abbreviated as: s, singlet; d, doublet; t, triplet; q, quartet; quint, quintet; sext, sextet; hept, heptet; br, broad; m, multiplet; or combinations thereof. High-resolution mass spectrometry (HRMS) was conducted using an Agilent 6224 Accurate-Mass time-of-flight (TOF) liquid-chromatography mass spectrometer (LC/MS) in combination with either atmospheric pressure chemical ionization (APCI) or electrospray ionization (ESI) methods. Fourier-transform infrared (FT-IR) spectra were recorded on a Thermo Scientific Nicolet 6700 FT-IR spectrometer referenced to a polystyrene standard. The signals are reported as frequency of absorption in wavenumbers ($cm^{-1}$) with descriptors abbreviated as: w, weak; m, medium; s, strong; br, broad. High-performance liquid chromatography (HPLC) purification was performed on an Agilent 1260 Infinity II LC with a reverse-phase (RP) Phenomenex Semi-preparative Column (00D-4439-E0 Gemini, C18 phase, 3 µm particle size, 110 Å pore size) with a flow rate of 8 mL/min and solvent mixtures of 0.1% formic acid (FA) in (A) acetonitrile (HPLC grade) and (B) water (HPLC grade). Optical rotation measurements were recorded on a Jasco P-2000 polarimeter with a Flint Glass Faraday cell modulator, sodium lamp light source, and photomultiplier tube (PMT) detector. Specific rotations were calculated based on the equation $[\alpha]=(100\cdot\alpha)/(l\cdot c)$ where the concentration c is in g/100 mL and the path length l is in decimeters. Calculated specific rotations are reported as unitless values and are represented as: $[\alpha]_D^T$ specific rotation (c concentration, solvent), where the temperature T is in ° C. and D stands for the sodium D-line monitor wavelength (589 nm).

Compound Synthesis and Characterization

Synthesis of L2

Methyl 6-O-Triphenylmethyl-α-D-mannopyranoside (2)

Trityl ether 2 was prepared following modified published procedures (Traboni et al., *ChemistrySelect* 2017, 2, 4906-4911; Tennant-Eyles et al., *J. Tetrahedron: Asymmetry* 2000, 11, 231-243). To a mixture of methyl-α-D-mannopyranoside (5.02 g, 25.8 mmol, 1.0 equiv) and trityl chloride (7.91 g, 28.4 mmol, 1.1 equiv) was added pyridine (5.2 mL, 64.6 mmol, 2.5 equiv). The reaction mixture was heated to 100° C. and stirred for 30 min. After 30 min, the resulting viscous paste was dissolved in CH$_2$Cl$_2$ by ultrasonication at 40° C. The solution was washed with saturated aqueous ammonium chloride (2×), dried over anhydrous sodium sulfate, filtered, and concentrated under reduced pressure. The crude residue was purified by flash column chromatography (50% to 100% ethyl acetate/hexanes) to afford 2 (11.0 g, 25.2 mmol, 98%) as a white foam. NMR spectra match those reported in the literature (Traboni et al., *ChemistrySelect* 2017, 2, 4906-4911; Tennant-Eyles et al., *J. Tetrahedron: Asymmetry* 2000, 11, 231-243). $^1$H NMR (400 MHz, CDCl$_3$) δ 7.48-7.28 (15H, m), 4.72 (1H, d, J=1.6 Hz), 3.92 (1H, m), 3.82-3.63 (3H, m), 3.50-3.39 (2H, m), 3.38 (3H, s), 2.73 (1H, m), 2.54 (1H, m), 2.27 (1H, m). $^{13}$C NMR (101 MHz, CDCl$_3$) δ 143.9, 128.9, 128.3, 127.5, 100.9, 87.7, 72.0, 70.64, 70.59, 70.1, 65.2, 55.3.

Methyl 2,3,4-Tri-O-benzyl-α-D-mannopyranoside (4)

Benzyl ether 3 was prepared according to a modified published procedure (Hofmann et al., *Carbohydr. Res.* 2015, 412, 34-42). Trityl ether 2 (2.01 g, 4.61 mmol) was dissolved in anhydrous DMF (115 mL) and to this solution was added portion-wise a suspension of NaH (60% in mineral oil, 14.8 g, 371 mmol, 7.2 equiv) at 0° C. The reaction mixture was stirred for 10 min at 0° C. and to this mixture was slowly added benzyl chloride (39.1 g, 309 mmol, 6.0 equiv) and the suspension was stirred for 5 min at 0° C. then warmed to rt and stirred for 16 h. The reaction mixture was quenched with water and extracted with ethyl acetate. The organic layer was dried over anhydrous sodium sulfate and concentrated under reduced pressure to afford 3 as a viscous yellow oil, which was used directly in the following procedure.

Alcohol 4 was prepared according to a modified published procedure (Jaramillo et al., *J. Org. Chem.* 1994, 59, 3135-3141). Benzyl ether 3 was dissolved in MeOH—CH$_2$Cl$_2$ (2:1, 6 mL) and p-TsOH was added until pH<4. The reaction mixture was stirred at rt for 20 h then neutralized with Et$_3$N and concentrated under reduced pressure. The residue was dissolved in CH$_2$Cl$_2$ and washed with distilled water and brine. The organic layer was dried over anhydrous sodium sulfate and concentrated under reduced pressure. The crude residue was purified by flash column chromatography (30% to 60% ethyl acetate/hexanes) to yield alcohol 4 (0.90 g, 1.94 mmol, 42%) as a light-yellow syrup. NMR spectra match those reported in the literature (Norberg et al., *Carbohydr. Res.* 2017, 452, 35-42). $^1$H NMR (CDCl$_3$, 400 MHz) δ 7.41-7.30 (15H, m), 4.97 (1H, d, J=10.9 Hz), 4.81 (1H, d, J=12.3 Hz), 4.75-4.65 (5H, m), 3.99 (1H, app. t, J=9.4 Hz), 3.92 (1H, dd, J=9.4, 2.9 Hz), 3.90-3.84 (1H, m), 3.83-3.76 (2H, m), 3.68-3.62 (1H, m), 3.33 (3H, s), 2.00 (1H, app. t, J=6.4 Hz). $^{13}$C NMR (101 MHz, CDCl$_3$) δ 138.8, 138.7, 138.6, 128.70, 128.68, 128.67, 128.3, 128.1, 128.0, 127.9, 99.6, 80.5, 75.5, 75.2, 75.0, 73.2, 72.5, 72.4, 62.7, 55.1. HRMS (APCI/LC-TOF) m/z: [M+NH$_4$]$^+$ Calcd for C$_{28}$H$_{32}$O$_6$ 482.2537; Found 482.2533.

Methyl 2,3,4-Tri-O-benzyl-6-deoxy-6-diethoxyphosphinylmethylene-α-D-mannopyranoside (7)

-continued

Aldehyde 5 was prepared according to a general procedure for oxidation of primary alcohols (Tojo et al., *Oxidation of alcohols to aldehydes and ketones: a guide to current common practice*. Springer Science & Business Media: 2006). A solution of 4 (0.334 g, 0.72 mmol, 0.4 M) was prepared in anhydrous DMSO (1.8 mL) under nitrogen. To this solution was added Et$_3$N (1.0 mL, 7.2 mmol, 10 equiv) and the reaction mixture was cooled to 0° C. in an ice water bath and stirred. To this solution was added dropwise a solution of sulfur trioxide-pyridine complex (0.347 g, 2.2 mmol, 3.0 equiv) in DMSO (1 mL) at 0° C. The reaction mixture was warmed to room temperature and stirred for 20 h. The solution was diluted with CH$_2$Cl$_2$ and washed with distilled water, dried over anhydrous sodium sulfate, and concentrated under reduced pressure to yield 5 as a yellow oil. The oil was filtered over a plug of silica and used directly in the following procedure.

Phosphonate 7 was prepared according to a modified published procedure (Vidil et al., *Eur. J. Org. Chem.* 1999, 447-450). To a suspension of NaH (60% in mineral oil, 37.8 mg, 0.945 mmol, 2.2 equiv) in anhydrous toluene (2 mL) was added dropwise tetraethyl methylenediphosphonate (0.27 mL, 1.08 mmol, 2.5 equiv) and stirred 30 min at rt. A solution of 5 in anhydrous toluene (5 mL) was added dropwise to this mixture under nitrogen and stirred at rt for 2 h. The reaction mixture was diluted with CH$_2$Cl$_2$ and quenched with distilled water. The organic layer was extracted with CH$_2$Cl$_2$ (3×), dried over anhydrous sodium sulfate, and concentrated under reduced pressure. The crude residue was purified by flash column chromatography (40% to 100% ethyl acetate/hexanes) to afford 7 as a colorless syrup (162 mg, 0.272 mmol, 62%). NMR spectra match those reported in the literature (Vidil et al., *Eur. J. Org. Chem.* 1999, 447-450). [α]$_D^{20}$=+40.4 (c=1.01, CHCl$_3$). $^1$H NMR (CDCl$_3$, 400 MHz) δ 7.39-7.27 (15H, m), 6.96 (1H, ddd, J=22.1, 17.2, 4.3 Hz), 6.12 (1H, ddd, J=21.2, 17.5, 1.8 Hz), 4.88 and 4.59 (2H, AM$_q$, J=10.6 Hz), 4.77 and 4.70 (2H, AB$_q$, J=12.4 Hz), 4.73 (1H, s), 4.63 (2H, s), 4.14-4.03 (5H, m), 3.90 (1H, dd, J=9.3, 3.0 Hz), 3.81-3.77 (1H, m), 3.72 (1H, t, J=9.5 Hz), 3.29 (3H, s), 1.31 (6H, t, J=7.1 Hz). $^{13}$C NMR (CDCl$_3$, 101 MHz) δ 148.4 (d, J=5.8 Hz), 138.7, 138.5, 138.3, 128.7, 128.4, 128.14, 128.05, 127.9, 118.3 (d, J=188.2 Hz), 99.6, 80.4, 78.5 (d, J=1.9 Hz), 75.7, 75.0, 73.2, 72.7, 71.5 (d, J=21.5 Hz), 62.1 (dd, J=5.8, 1.3 Hz), 55.3, 16.7. $^{31}$P NMR (162 MHz, CDCl$_3$) δ 18.3. FT-IR (neat, cm$^{-1}$): ν(C—H)=2982 (m), ν(P=O)=1253 (s), ν(P—O—C)=1024 (s), ν(P—O—C)=969 (m).

Methyl 2,3,4-Tri-O-benzyl-6-deoxy-6-diisopropyloxycarbonyloxy-methyl-phosphinylmethylene-α-D-mannopyranoside (10)

Phosphonic acid 8 was prepared according to a published procedure (Vidil et al., *Eur. J. Org. Chem.* 1999, 447-450). To a solution of 7 (0.146 g, 0.245 mmol, 1 equiv) in anhydrous CH$_3$CN (5.6 mL) under nitrogen was added pyridine (31 μL, 0.392 mmol, 1.6 equiv) and trimethylsilyl bromide (0.32 mL, 2.45 mmol, 10 equiv) with stirring at room temperature. After 2 h, the reaction mixture was cooled to 0° C. and was added pyridine (51 μL, 0.634 mmol, 2.6 equiv) and H$_2$O (185 μL, 10.3 mmol, 42 equiv) then warmed to rt and stirred. After 2 h, the reaction mixture was diluted with CH$_2$Cl$_2$ and 2 M HCl (4 mL) and H$_2$O (4 mL). The organic layer was extracted with CH$_2$Cl$_2$, dried over anhydrous sodium sulfate, and concentrated under reduced pressure to yield 8 as a brown oil. The crude residue was used directly in the following procedure.

Phosphonate 10 was prepared following a modified procedure (Graham et al., (2017). International Patent Appl. Publication No. WO2017/87256). A mixture of 8 in anhydrous CH$_3$CN under nitrogen was treated with DIPEA (0.480 mL, 2.76 mmol, 9.9 equiv), TBAB (93.1 mg, 0.289 mmol, 1.0 equiv), and chloromethyl isopropyl carbonate (0.30 mL, 2.24 mmol, 8.1 equiv) then was heated to 60° C. After stirring for 16 h, the reaction mixture was concentrated under reduced pressure. The crude residue was purified by flash column chromatography (30% to 100% ethyl acetate/hexanes) to yield 10 as a colorless oil (116 mg, 0.150 mmol, 54%). TLC (EtOH/EtOAc/hexanes 1.5:1.5:7): $R_f$=0.49. $^1$H NMR (CDCl$_3$, 400 MHz) δ 7.40-7.29 (15H, m), 7.10 (1H, ddd, J=24.5, 17.2, 3.8 Hz), 6.40-6.17 (1H, m), 5.80-5.65 (6H, m), 4.81-4.59 (7H, m), 4.22-4.14 (1H, m), 3.91 (1H, dd, J=9.3, 3.1 Hz), 3.83-3.78 (1H, m), 3.74 (1H, t, J=9.5 Hz), 3.30 (3H, s), 1.32-1.29 (12H, m). $^{13}$C NMR (CDCl$_3$, 101 MHz) δ 153.5, 138.7, 138.5, 138.3, 128.8, 128.7, 128.6, 128.2, 128.1, 127.9, 99.7, 84.5 (d, J=5.7 Hz), 84.4 (d, J=6.8 Hz), 80.5, 78.3 (d, J=2.1 Hz), 75.8, 75.0, 73.5 (d, J=3.5 Hz), 73.3, 72.7, 71.3 (d, J=22.3 Hz), 55.3. $^{31}$P NMR (162 MHz, CDCl$_3$) δ 26.3.

Methyl 6-Deoxy-6-diisopropyloxycarbonyloxy-methyl-phosphinylmethyl-α-D-mannopyranoside (L2)

The final step in the synthesis of L2 was performed according to a published hydrogenation procedure (Jeanjean et al., *Bioorg. Med. Chem. Lett.* 2008, 18, 6240-6243). In an oven-dried vial 10 (36.0 mg, 0.047, 1 equiv) was dried and degasses under high vacuum. To this was added 10% Pd/C (36.6 mg, 0.344 mmol, 7.4 equiv) and rinsed down with CH$_2$Cl$_2$ (2 mL) and EtOH (2 mL). The reaction mixture was subsurface sparged with N$_2$ for 1 min. The reaction mixture was then degassed under reduced pressure and the atmosphere was replaced by H$_2$ (5×). The reaction mixture was stirred vigorously under H$_2$ for 4 h, after which time the reaction mixture was degassed under reduced pressure and refilled with N$_2$ (5×). The reaction mixture was diluted with CH$_2$Cl$_2$ (2 mL) and filtered over a plug of wet celite. The filtered organic layer was concentrated under reduced pressure and the crude residue was purified by HPLC (40% to 85% [H$_2$O+0.1% FA]:[CH$_3$CN+0.1% FA], $t_R$(L2)=7.00 min) to afford L2 (10.1 mg, 0.020 mmol, 43%) as a white solid. All $^{13}$C-$^{31}$P coupling constants are within the standard range of values (Buchanan et al., *Can. J. Chem.* 1976, 54, 231-237). $^1$H NMR (400 MHz, CDCl$_3$) δ 5.68 (2H, dd, J=20.5 Hz, J=5.3 Hz, H8), 5.65 (2H, dd, J=18.3 Hz, J=5.4 Hz, H8'), 4.93 (2H, hept, J=6.3 Hz, H10), 4.68 (1H, s, H1), 3.95-3.86 (1H, br, H5), 3.74 (1H, m, H2), 3.58 (2H, m, H3, H4), 3.35 (3H, s, OCH$_3$), 3.22-3.07 (1H, m, OH), 2.95 (2H, m, 2×OH), 2.27-2.07 (2H, m), 2.06-1.86 (2H, m, H6, H6', H7, H7'), 1.32 (12H, d, J=6.2 Hz, H11). $^{13}$C NMR (101 MHz, CDCl$_3$) δ 153.6 (d, J=3.7 Hz, C9), 101.2 (s, C1), 84.5 (d, J=6.3 Hz, C8), 84.3 (d, J=6.3 Hz, C8'), 73.7 (d, J=3.2 Hz, C10), 72.0 (s, C2), 70.9 (d, J=16.1 Hz, C5), 70.6 (s), 70.5 (s, C3, C4), 55.3 (s, OCH$_3$), 23.8 (d, J=4.5 Hz, C6), 22.4 (s, C11), 21.7 (d, J=142.3 Hz, C7). $^{31}$P NMR (162 MHz, CDCl$_3$) δ 34.4. FT-IR (neat, cm$^{-1}$): ν(O—H)=3409 (br), ν(C—H)=2923 (m), ν(C═O)=1760 (s), ν(P═O)=1269 (s). LR-MS (ESI−) calcd for [M+HCOO]$^-$: 549.2; found: 549.2.

While the present invention has been described through illustrative embodiments, routine modification will be apparent to those skilled in the art and such modifications are intended to be within the scope of this disclosure.

What is claimed is:

1. A compound that has the structure:

2. A pharmaceutically acceptable salt of a compound that has the structure:

3. A pharmaceutical composition comprising the compound of claim 1 and one or more pharmaceutically acceptable excipients.

4. A pharmaceutical composition comprising the pharmaceutically acceptable salt of the compound of claim 2 and one or more pharmaceutically acceptable excipients.

\* \* \* \* \*